United States Patent [19]

Szaantay et al.

[11] 4,133,812
[45] Jan. 9, 1979

[54] PROCESS FOR PRODUCING BENZO (A) QUINOLIZINE DERIVATIVES

[75] Inventors: Csaba Szaantay; Jaanos Rohaaly; Istvaan Jelinek, all of Budapest, Hungary

[73] Assignee: Chinoin Gyogyszer es Vegyeszeti Termekek Gyara Rt., Budapest, Hungary

[21] Appl. No.: 790,538

[22] Filed: Apr. 25, 1977

Related U.S. Application Data

[63] Continuation of Ser. No. 634,274, Nov. 21, 1975, abandoned, which is a continuation-in-part of Ser. No. 372,425, Jun. 21, 1975, abandoned.

[51] Int. Cl.$^2$ ............................................. C07D 455/08
[52] U.S. Cl. ........................................ 546/96; 546/95; 424/274
[58] Field of Search ...................... 260/288 CF, 288 E

[56] References Cited

U.S. PATENT DOCUMENTS

| 2,877,226 | 3/1959 | Brossi et al. | 260/288 CF |
| 3,045,020 | 7/1962 | Battersby | 260/288 CF |
| 3,132,147 | 5/1964 | Schopf | 260/288 CF |
| 3,359,264 | 12/1967 | Gerache | 260/288 CF |

FOREIGN PATENT DOCUMENTS

| 217920 | 5/1957 | Australia | 260/288 CF |
| 197383 | 4/1958 | Austria | 260/288 CF |

Primary Examiner—Donald G. Daus
Assistant Examiner—Mary C. Vaughn
Attorney, Agent, or Firm—Karl F. Ross

[57] ABSTRACT

Compounds are prepared with anti-amoeba activity of the following formula:

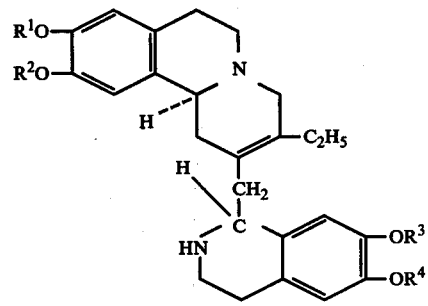

wherein $R^1$ equals $R^2$ and each is lower alkyl and $R^3$ and $R^4$ are each lower alkyl, with the proviso that $R^1$ and $R^2$ are not methyl and $R^3$ and $R^4$ are not both ethyl.

2 Claims, No Drawings

PROCESS FOR PRODUCING BENZO (A) QUINOLIZINE DERIVATIVES

CROSS REFERENCE TO RELATED APPLICATIONS

This application is a continuation of Ser. No. 634,274 (now abandoned), filed Nov. 21, 1975 as a continuation-in-part of U.S. application Ser. No. 372,425 filed June 21, 1975 now abandoned.

FIELD OF THE INVENTION

This invention relates to compounds capable of treating amoebiasis and having an amoebicidal effect when used in the treatment of mammalia, especially man. More particularly, this invention relates to compounds of the type

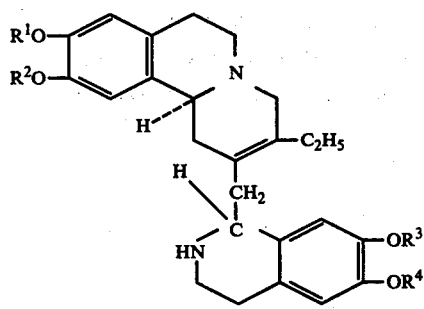

wherein $R^1$ and $R^2$ are the same and each is lower alkyl and $R^3$ and $R^4$ are each lower alkyl, with the proviso that $R^1$ and $R^2$ are not methyl and $R^3$ and $R^4$ are not both ethyl, and especially to compounds of the following type

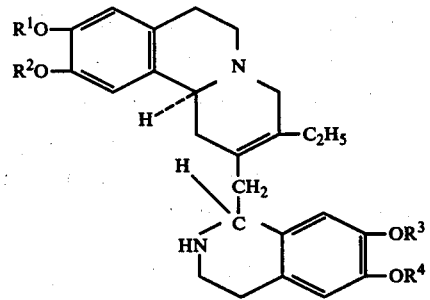

wherein $R^1$ and $R^2$ are the same and each is lower alkyl and $R^3$ and $R^4$ are each lower alkyl, with the proviso that $R^3$ is not the same as $R^4$. The invention also relates to methods of making these compounds, pharmaceutical compositions containing these compounds and to a method of treating a patient suffering from an amoebic disorder.

OBJECTS OF THE INVENTION

The present invention has as its principal object the provision of a compound or class of compounds having greater effectiveness than emetine or dehydroemetine for the treatment of amoebic disorders.

Another object of the invention is to provide a method of making a new and more effective compound for the treatment of amoebic disorders and having amoebicidal characteristics.

It is also an object of the invention to provide a method of treating mammalian subjects, e.g. human patients, for amoebic disorders.

SUMMARY OF THE INVENTION

In the course of the investigations of the different benzoquinolizidine derivatives it was found, that the lethal dose $LD_{50}$ of the new benzoquinolizidine derivative of the formula Ia

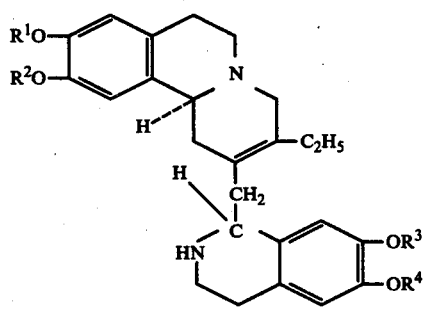

wherein $R^1$ is the same as $R^2$ and each is lower alkyl and $R^3$ and $R^4$ are each lower with the proviso that $R^1$ and $R^2$ are not methyl and $R^3$ and $R^4$ are not both ethyl.

The activity against entamoeba hystolytica strains of the derivative of the formula Ia of the emetine and of the dehydroemetine is about the same, thus the therapeutical index of the new compound is 10–12-times better.

The present invention is directed to the new compound of the formula Ia and to the new preparation of the compounds of the formula I

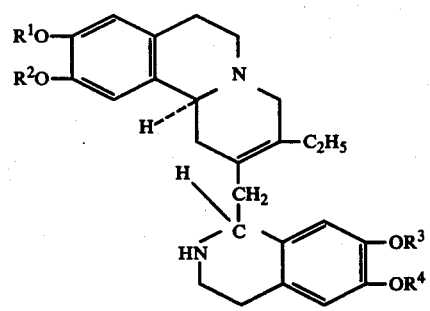

wherein $R^1$ is the same as $R^2$ and each is lower alkyl and $R^3$ and $R^4$ are each lower alkyl, with the proviso that $R^3$ differs from $R^4$.

A preferred feature of the invention includes compounds with the formula:

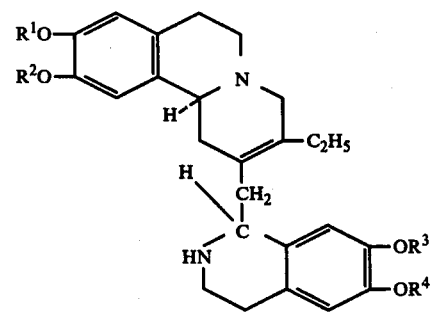

wherein R is lower alkyl and $R^3$ and $R^4$ are each lower alkyl, with the proviso that $R^3$ differs from $R^4$.

The difference between the first formula I and the latter is that $R=R^1$ and/or $R^2$, where R is lower alkyl and $R^3$ and $R^4$ are not both ethyl or methyl when R is methyl and R is not ethyl when $R^3$ and $R^4$ are both ethyl. Generally herein the preferred lower alkyls are $C_1-C_4$ alkyl and most preferably the straight-chain modalities.

As a starting step for the preparation of the compounds of the formula I, the compound 6,7-dialkoxy-3,4-dihydro-isoquinoline is reacted with 2-ethyl-butene-1-one-3 by a method known per se Beke D., Szantay Cs.: Chem. Ber. 95, 2132, 1962. The ketone of the formula II

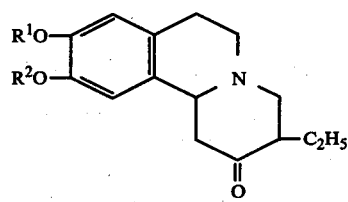

thus obtained, wherein $R^1$ and $R^2$ are defined above, is reacted with carbalkoxy-methyl-phosphonic acid diethyl ester according to the Hungarian Patent Specification No. 151,195 and thus the unsaturated ester of the formula III

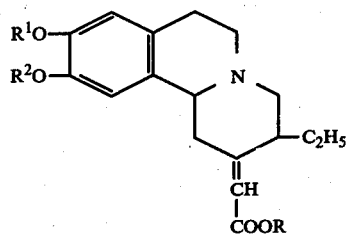

is obtained, wherein $R^1$ and $R^2$ are defined above and R is alkyl, particularly for a methyl or ethyl group.

The exocyclic double bond of the compound of the formula III is isomerized with sodium alcoholate N. Whittaker: J. Chem. Soc. (C) 1969, 94, but there are other methods for forming compounds of the formula IV

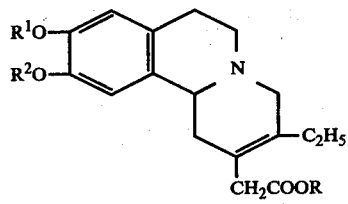

from the compounds of the formula III, e.g. UV irradiation. The photochemical isomerization of the double bond may be advantageously carried out by hydrolyzing the ester of the formula III to free acid, by UV irradiation in a methanol solution, or by esterificating again to obtain the compound of the formula IV, wherein $R^1$, $R^2$ and R are defined above.

According to a feature of the present invention a compound of the formula IV is reduced to the compound of the formula V

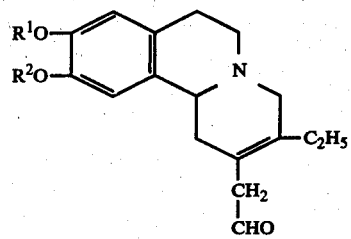

with diisobutyl-aluminum-hydride, wherein $R^1$ and $R^2$ are defined above, and the compound thus obtained is condensed with β-(3-hydroxy-4-alkoxyphenyl)-ethylamine and the compound of the formula VI

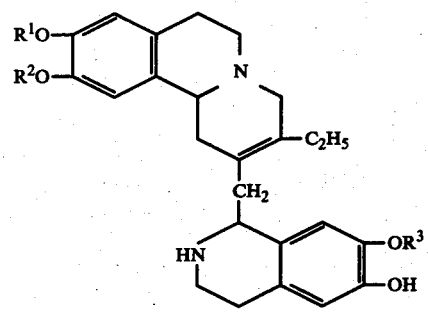

is alkylated to give the compound of the formula I.

When preparing the compound of the formula Ia the ethylation is carried out with diazoethane, or with the equivalent mixture of diethyl sulphate and alkali.

Besides the compound of the formula I, the epimer compound thereof of the formula VII

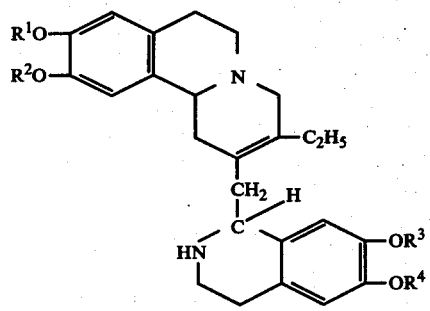

having lower antiamoebic activity, may be isolated.

The compounds of the formula I may also be prepared by reducing O-alkyl-2-dehydro-psychotrine of the formula VIII

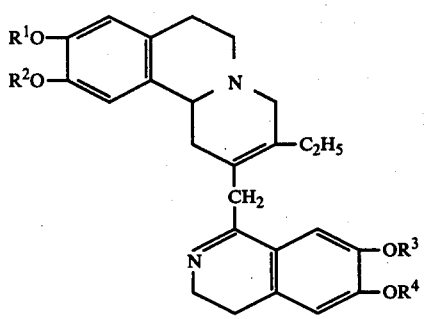

The reduction may be carried out in an acidic medium with the aid of zinc, iron or tin Hungarian Patent Specification No. 152 454 or by catalytic hydrogenation in the presence of platinaoxide catalyst Helv. Chim. Acta. Vol. XLII. 1959, pp 783–785.

The compounds of the formula I according to the present invention may be formulated optionally by adding pharmaceutically acceptable carriers or excipients in the form of capsules, tablets, dragees, enterosolvent dragees, suspensions, granules or in the form of premix.

EXAMPLE 1a 25.57 g. 0.1 mole of 6,7-diethoxy-3,4-dihydro-isoquinoline hydrochloride salt and 14.47 g. 0.147 moles of 2-ethyl-butent-1-one-3 are mixed and the mixture is heated on a waterbath under reflux in 75.0 ml. of 93% ethyl alcohol for 24 hours. The alcohol is distilled off. The residue dissolved in water, is alkalized with solid sodium carbonate and is allowed to stand in a refrigerator through one night. The precipitated crystals are sucked free from the filtrate, washed with 2×20 ml. of cold water and dried. Thus 25.0 g. of the product are obtained, m.p.: 115°–118° C. After recrystallization from 50 ml. of acetone 19.3 g. 62% of 2-oxo-3-ethyl-9,10-diethoxy-1,2,3,4,6,7-hexahydro-11bH-benzo(a)-quinolizine are obtained in the form of white crystals, m.p.: 120°–122° C. described m.p.: 117°–118° C.

$UV_{max.}^{EtOH}$ (log): 212 nm. 4.045, 281, 3.474; at 224 nm. inflexion, IR (KBR): Bohlmann bands at 2760 and 2800 cm.$^{-1}$

EXAMPLE 1b 2.32 g. (0.06 g.atoms) of metallic potassium are dissolved in 10 ml. of water-free benzene and 30 ml. of water-free tertiary butanol. The solution is evaporated in vacuo in a dry nitrogen current. 16.0 g. (0.076 moles) of methoxycarbonyl-methyl-phosphonic acid diethyl-ester and 19.2 ml. of water-free dimethyl formamide are added to the dry potassium tertiary butylate residue. When the potassium tertiary butanol is dissolved-1,2,3,4,6,7-hexahydro-11bH-benzo(a)quinolizine, dissolved in 42.5 ml. of water-free dimethyl formamide are added to the solution of room temperature and the mixture is allowed to stand at room temperature for 72 hours. The mixture is dropped into 500 g. of icy water and the aqueous phase is shaken for 15 minutes with 20 ml. of saturated sodium hydrogen sulphite solution and then with 2×50 ml. of water. The ether solution is dried with magnesium sulphate, filtered and evaporated. The residue is 10.15 g. (99%) of a resinous substance. The residue is dissolved in 6.5 ml. of methyl alcohol, and is allowed to stand for one night in a refrigerator. The product is precipitated in the form of light-yellow crystals. The yield is 8 g. (80%) of 2-methoxy-carbonyl-methylene-3-ethyl-9,10-diethoxy-1,2,3,4,6,7-hexahydro-11bH-benzo(a)quinolizine, mp.: 77°–78° C.

Analysis for the formula $C_{22}H_{31}NO_4$:
Calculated: C=70.75%; H=8.37%; N=3.75%
Found: C=70.80%; H=8.35%; N=3.81%.

IR (KBr) (Bohlmann bands): 2745, 2765 and 2805 cm.$^{-1}$ weak CO 1720 cm.$^{-1}$, >C=C—CO—OR 1640 cm.$^{-1}$

EXAMPLE 1c 4.5 g. of 2-methoxycarbonylmethylene-3-ethyl-9,10-diethoxy-1,2,3,4,6,7-hexahydro-11bH-benzo(a)quinolozine are dissolved in 10 ml. of anhydrous methanol. After addition of 1.67 g. of metal sodium in 25 ml of anhydrous methanol, the mixture is heated under nitrogen atmosphere for 2 hours. The methanol is distilled off, the residue is admixed with water, extracted with benzene and the benzene solution is evaporated to dryness in vacuo. 2.6 g. of the oily residue (4.5 g., 100%) are dissolved in 50 ml. of anhydrous toluene, whereupon 1.2 g. of diisobutyl-aluminum hydride are added under nitrogen at −65° C. After 2 hours 40 ml. of aqueous saturated sodium disulphite solution are added, the precipitate is filtered at room temperature, dissolved in 100 ml. of water and extracted with 40 ml. of ether. The aqueous solution is alkalized to pH = 9 with 2 n sodium hydroxide under cooling and extracted with ether. After evaporating the solvent, the residual aldehyde and 1.7 g. of β-(3-hydroxy-4-ethoxyphenyl)-ethylamine-hydrochloride are admixed with 36 ml. of water, and 3 ml. of glacial acetic acid are added. The pH value of the clear solution is 4.5. The mixture is allowed to stand for five days, and the pH is adjusted to 9 with solid sodium carbonate; the precipitated yellow substance is filtered, washed and dried in a vacuum desiccator; the substance is dissolved in 40 ml. of ethanol and 200 ml. of ether solution, containing 3.g. of diazoethane are added. After 2 days the ether is distilled off and the residue is again dissolved in ether and is shaken out with 2 n sodium hydroxide solution and with water. After drying, the ether is distilled off. The residue is 1.55 g. containing a mixture of the compound of the formula Ia and the compound of the formula VII (the corresponding 1' epimer compound of the compound of the formula Ia)

EXAMPLE 1d

The separation of the compound of the formula Ia and of the corresponding epimer of the formula VII 3.72 g. of the mixture of the hydrochloride salts of the compounds of the formula Ia and the corresponding formula VII are dissolved in 17.5 ml. of methyl alcohol; the solution is admixed with 35.5 ml. of ether and the solution is allowed to stand in a refrigerator. The methyl alcohol-ether mother liquor is poured down from the white crystals being at the bottom and on the walls of the vessel. The crystals are washed and are dried with a mixture of methyl alcohol (cooled to 0° C.): ether in a proportion of 1:2 over calcium chloride in a vacuum desiccator. Thus 1.52 g. (0.0024 moles, 42%) of (6,7-diethoxy-1,2,3,4-tetrahydro-1-isoquinolyl)-methyl-3-ethyl-1,4,6,7-tetrahydro-9,10-diethoxy-11bH-benzo(a)quinolizine. 2HCl.H$_2$O are obtained, the product melts at 210°–212° C. (decomposition).

Analysis for the formula: $C_{33}H_{46}N_2O_4.2HCl.H_2O$ (625.66):

Calculated C=63.34%; H=8.06%; H=4.40% Cl=11.34% H₂O=2.88% Found: C=63.48%; H=8.30%; N=4.40%; Cl=11.11%; H₂O=2.96%.

IR (KBr): NH₂ 2600 cm.⁻¹

UV$_{max}^{H_2O}$ (log): 213 nm. (4.19), 230 (4.09), 282.5 (3.798)

1 g. (0.0016 moles) of the compound of the formula VII.2HCl.H₂O is dissolved in 10 ml. of water and is alkalized under cooling with icy water with concentrated ammonium hydroxide. The white precipitate is washed with water and dried in vacuum desiccator over potassium hydroxide. Thus 0.7 g. of amorphous white racemis 2μ ethoxy-dehydro-emetine" (VII) are obtained.

Analysis for the formula C₃₃H₄₆N₂O₄.½ H₂O
Calculated: C=72.88%; H=8.62%; N=5.15%; H₂O=1.65% Found: C=73.05%; H=8.48%; N=5.19%; H₂O=1.52%.

EXAMPLE 2a 2.6 g. (7.25 m moles) of 3-ethyl-9,10-dimethoxy-1,4,6,7-tetrahydro-11bH-benzo(a)quinolizine-2-acetic acid-ethyl ester are dissolved in 53 ml. of water-free toluene. The solution is cooled while stirring in a nitrogen stream to −65° C. 1.2 g. (1.5 ml., 8.5 moles) of diisobutyl-aluminum hydride are added to the solution and the temperature is kept for 2 hours at −65° C. and the mixture is stirred. 40 ml. of saturated sodium bisulphite is dropped to the solution with a speed that the temperature of the solution should not rise above −40° C. After the addition of the sodium bisulphite solution the temperature of the solution is allowed to rise to room temperature. The precipitate thus obtained is filtered and dissolved in 100 ml. of water.

The toluene is separated from the aqueous sodium bisulphite solution. The aqueous parts are united and extracted with 40 ml. of ether. Whereupon the aqueous part is alkalized to pH=9 with 2 n sodium hydroxide solution while cooling with a salt-ice system, the temperature of the solution being held to a maximum of 0° C. The separated precipitate is solved into 60 ml. of ether, and the aqueous part is extracted with further 3×30 ml. of ether. The united ether solution is dried over magnesium sulphate; the ether is filtered and distilled off at room temperature in vacuo in a nitrogen current. The residue contains 1.4 g. (4.45 m moles, 61.5%) of racemic 2,3-didehydro-protoemetine, the product is a solid white beige colored substance.

PMR (CdCl₃)(inert standard is tetramethyl silane).

| Chemical Displacement | Values |
|---|---|
| C-3 ethyl group | 1.04 triplet |
| C-9 and c-10 CH₃ | 3.84 |
| C-8 aromatic H | 6.58 |
| C-11 aromatic H | 6.61 |
| C-2 aldehyde H | 9.68 |

0.15 g. (0.475 m moles) of racemic 2,3-didehydro-protoemetine are dissolved in 1 ml. of ethyl alcohol and 0.17 ml of 70% perchloric acid are added by drops to the solution, whereupon the perchloric acid salt is precipitated with water. Thus 1.175 g (0.395 m moles) of racemic 2,3-didehydro-protoemetine perchloric acid salt are obtained. The salt is dissolved in 3.2 ml of methyl alcohol under heating whereafter the solution is cooled to room temperature and a few drops of water are added until the solution becomes cloudy and the mixture is allowed to stand in a refrigerator. Thus 0.076g. (0.17 m moles) of crystallized rac.-2,3-didehydro-protoemetine-perchloric acid salt.H₂O are obtained, m.p.: 198°-200° C.

Analysis for the formula: C₁₉H₂₅NO₃.HClO₄.H₂O
Calculated: C=52.6% H=6.506% N=3.32% Cl=8.17%, H₂O=4.52% Found: C=52.11% H=6.60% N=3.13% Cl=7.82%, H₂O=4.15%

EXAMPLE 2b 1.3 g. (4.15 m moles) of rac.-2,3-didehydro-protoemetine and 1.71 g. (8.15 m moles) of β-(3-hydroxy-4-methoxy-phenyl)-ethylamine-hydrochloric-acid salt are admixed in 36 ml. of water and 3 ml. of glacial acetic acid are added. The solution (pH=4.5) is allowed to stand at room temperature under nitrogen for five days. The pH value of the solution is adjusted to 9 by adding solid sodium carbonate. Light brown precipitate is obtained, it is filtered, washed with water and dried over phosphorous pentoxide in a vacuum desiccator. 1.55 g. (3.35 m moles, 81%) of crude rac.-2,3-didehydro-cephaeline are obtained.

EXAMPLE 2c 1.77 g. (3.8 m moles) of rac.-d,3-didehydro-cephaeline are dissolved in 40 ml. of ethyl alcohol and 300 ml. of ether solution, containing 3.5 g. (83.5 m moles) of diazomethane are added. The solution is allowed to stand at room temperature for two days. The ether and the alcohol are distilled off in vacuo using a water bath of a temperature max. 35° C. The residual oily substance is dissolved in 75 ml. of ether, the undissolved part is filtered and the filtrate is shaken out with 1×20 ml. of 2 n sodium hydroxide solution and 5×20 ml. of water and the mixture is dried over magnesium sulphate. The ether solution is filtered and the ether is distilled off in vacuo. As a residue a solid substance is obtained, 1.55 g. (3.24 m moles, 85%) of a mixture of rac.-2,3-didehydro-emetine and rac.-2,3-didehydro-isoemetine in a proportion of 1:1.

The mixture is dissolved in 2.7 ml. of methyl alcohol and 0.81 g. (9 m moles) of anhydrous oxalic acid in 1.6 ml. of methyl alcohol are added to the rac.-2,3-dehydro-isoemetine, whereafter the mixture is allowed to stand for one day at room temperature. 1 g. (1.5 m moles) of crystallized rac.-2,3-didehydro-isoemetine-oxalic-acid salt is obtained. Mp.: 175°-177° C. (described m.p.: 175°-178° C.: Brossi et al.: Helv.Chim. Acta. 42, 783, 1953).

The filtered solution is evaporated in vacuo, the residue is dissolved in 20 ml. of water, clarified with charcoal and is alkalized with 1 ml. of 10 n sodium hydroxide solution. The precipitated solid substance is solved into 40 ml. of benzene and is separated from the aqueous phase. The benzene solution is extracted with 3×20 ml. of water, dried over magnesium sulphate, filtered and acidified with hydrochloric ethyl alcohol, whereafter the solution is evaporated to dryness in vacuo and by crystallization of the residue (0.9 g.) from the mixture of 15 ml. of methyl alcohol and 40 ml. of ether 0.8g. (1.38 m moles, 36.5%) of rac.-2,3-didehydro-emetine-dihydrochloric acid salt are obtained, m.p.: 252°-254° C.

EXAMPLE 3

1.5 g (0.0120 moles) of 2-methoxycarbonylmethylene-3-ethyl-9,10-diethoxy-1,2,3,4.6,7-hexahydro-11bH-benzo(a)quinolizine are dissolved in 10 ml of anhydrous methanol. After addition of 1.67 g of sodium metal in 25 ml of anhydrous methanol, the mixture is heated under a nitrogen atmosphere for 2 hours.

The methanol is distilled off; the residue is admixed with water, extracted with benzene and the benzene solution is evaporated to dryness in vacuo. 2.6 g of the oily residue are dissolved in 50 ml of anhydrous toluene, whereupon 1.2 g of diisobutyl-aluminum-hydride are added under nitrogen at 65° C. After 2 hours 40 ml of aqueous saturated sodium disulphite solution are added; the precipitate is filtered off at room temperature, dissolved in 100 ml of water and extracted with 40 ml of ether.

The aqueous solution is made alkaline with 2 n sodium hydroxide under cooling and extracted with ether. After evaporating the solvent, the residual aldehyde and 1.54 g (0.0079 moles) β-(3-hydroxy-4-methoxy-phenyl)-ethylamine-hydrochloride are admixed with 36 ml of water and 3 ml of glacial acetic acid are added. The pH value of the clear solution is 4.5.

The mixture is allowed to stand for five days, and the pH is adjusted to 9 with solid sodium carbonate; the precipitated substance is filtered, washed and dried in a vacuo desiccator. The substance is dissolved in 40 ml of ethanol and 200 ml of ether solution containing 3 g of diazoethane are added. After 2 days the ether is distilled off and the residue is again dissolved in ether and shaken out.

The residue amounts to 1.55 g (0.003 moles) and contains a mixture of (6'-ethoxy-7'-methoxy-1',2',3',4'-tetrahydro-1'-isoquinolyl)-methyl-3-ethyl-1,4,6,7-tetrahydro-9,10-diethoxy-11bH-benzo(a)quinolizine (Compound A) and its 1' epimer compound. The mixture of the hydrochloride salts of the compounds above is dissolved in 10 ml of methyl alcohol; the solution is admixed with 30 ml of ether and the solution is allowed to stand in a refrigerator.

The crystals are washed and are dried with a mixture of methyl alcohol cooled to 0° C.: ether in a proportion of 1:3 over calcium chloride in a vacuum desiccator. Thus 0.672 g (0.0011 moles) of (6'-ethoxy-7'-methoxy-1',2',3',4'-tetrahydro-1'-isoquinolyl)-methyl-3-ethyl-1,4,6,7-tetrahydro-9,10-diethoxy-11bH-benzo(a)-quinolizine 2 HCl.H$_2$O are obtained; the product melts at 218°–220° C.

Analysis for the formula C$_{32}$H$_{44}$N$_2$O$_4$.2HCl.H$_2$O (611.622):

Calculated: C=62.84%; H=7.91%; N=4.58%; Cl=11.06%; H$_2$O=2.95% Found: C=62.63%; H=7.98%; N=4.80%; Cl=12.0%; H$_2$O=2.5%

IR/KBr 2600–2500 NH$_2$$^{(+)}$

UV$_{max}$$^{H2O}$ (log) 210 nm (4.00) 228 (3.95) 280/3.75.

EXAMPLE 4

The process according to Example 3 is carried out except that alkylating is effected with 200 ml of ether solution, containing 2.18 g of diazomethane. 1.42 g, containing a mixture of (6',7'-dimethoxy-1',2',3',4'-tetrahydro-1'-isoquinolyl)-methyl-3-ethyl-1,4,6,7-tetrahydro-9,10-diethoxy-11bH-benzo(a)quinolizine (Compound B) and its 1' epimer compound are obtained. The mixture of the hydrochloride salts of the compounds above is separated according to Example 3. Thus 0.55 g. (0.9 m moles) 6',7'-dimethoxy-1',2',3',4'-tetrahydro-1'-isoquinolyl-methyl-3-ethyl-1,4,6,7-tetrahydro-9,10-diethoxy-11bH-benzo(a)quinolizine.2HCl.2,5H$_2$O are obtained; the product melts at 206°–208° C. (decomposition).

Analysis for the formula C$_{31}$H$_{42}$N$_2$O$_4$.2HCl2,5H$_2$O (622.62):

Calculated: C=59.80%; H=7.61%; N=4.50%; Cl=11.39%; H$_2$O=7.16% Found: C=60.07%; H=7.72%; N=4.32%; Cl=10.95%; H$_2$O=6.95%

IR (KBr) 2612

UV$_{max}$$^{H2O}$ (log) 210 nm (4.01) 230 (3.89) 280 (3.84)

EXAMPLE 5

1.3 g (4.15 m moles) of rac.-2,3-dihydro-protoemetine and 1.75g (8.3 m moles) of β-(3-hydroxy-4-ethoxy-phenyl)-ethylaminehydrochloric-acid salt are admixed in 36 ml of water and 3 ml of glacial acetic acid are added. The solution (pH = 4.5) is allowed to stand at room temperature under nitrogen for five days. The pH value of the solution is adjusted to 9 by adding solid sodium carbonate. The precipitate is filtered, washed with water and dried in a vacuum desiccator. The substance is dissolved in 40 ml of ethanol and 260 ml of ether solution, containing 3 g of diazomethane, is added. After 2 days the ether is distilled off and the residue is again dissolved in ether and shaken out with 2 n sodium hydroxide solution and with water. After drying the ether is distilled off. The residue is 1.45 g (0.00295 moles), containing a mixture of 6'-methoxy-7'-ethoxy-1',2',3',4'-tetrahydro-1'-isoquinolylmethyl-3-ethyl-1,4,6,7-tetrahydro-9,10-dimethoxy-11bH-benzo(a)-quinolizine (Compound C) and its 1' epimer compound.

The mixture of the hydrochloride salts of the compounds above is dissolved in 15 ml of methyl alcohol; the solution is admixed with 40 ml of ether and the solution is allowed to stand in a refrigerator. The crystals are filtered and dried over calcium chloride in a vacuum desiccator. Thus 0.655 g (0.0011 moles) of 6'-methoxy-7'-ethoxy-1',2',3',4'-tetrahydro-1'-isoquinolyl-methyl-3-ethyl-1,4,6,7-tetrahydro-9,10-dimethoxy-11bH-benzo(a)quinolizine.2HCl/2 H$_2$O are obtained; the product melts at 224°–226° C.

Analysis for the formula C$_{30}$H$_{40}$N$_2$O$_4$2HCl ½ H$_2$O (574.57):

Calculated: C=62.76%; H=7.35%; N=4.88%; Cl=12.35%; H$_2$O=1.57% Found: C=62.51%; H=7.70%; N=4.60%; Cl=12.5%; H$_2$O=1.20%.

IR (KBr): NH$_2$ 1650–1550 cm$^{-1}$.

The pharmaceutical compositions may be finished in the form of eye drops, expectorants, cough mixtures, injections, etc., by usual methods of the pharmaceutical industry.

| Preparation of Injectable Compositions | |
|---|---|
| Volume: | 5 ml |
| Active ingredient (Compound A) content | 50 mg |
| Active Ingredient (Compound A) | 100 g |
| Sodium Chloride | 75 g |
| 0.1 N hydrochloric acid or 0.1 N sodium hydroxide ad pH | 2.7–3.2 |
| Distilled water for injection purposes ad | 10,000 ml. |

The active ingredient and thereafter the sodium chloride is dissolved in oxygen-free distilled water. After complete dissolution to about 9500 ml of the solution 0.1 N hydrochloric acid or 0.1 N sodium hydroxide is added to adjust the pH to the value of 2.7–3.2. Thereafter the volume of the solution is adjusted to 10,000 ml with oxygen-free distilled water, the solution is filtered to obtain a completely clear filtrate and filled under nitrogen into brown-tinted 5 ml ampoules. Sterilization is carried out at 100° C. for an hour.

| Preparation of Injections | |
|---|---|
| Active Ingredient (Compound A) | 150.0 g |
| Sodium Acetate | 55.0 g |
| Sodium pyrosulfite | 10.0 g |
| 0.1 N hydrochloric acid ad to pH | 3.0–3.2 |
| Distilled water for injection purposes ad | 10,000 ml. |

The sodium pyrosulfite, sodium acetate and thereafter the active ingredient are dissolved in oxygen-free distilled water. After complete dissolution the pH of the solution (volume about 9500 ml) is adjusted to 3.0–3.2 by adding 0.1 N hydrochloric acid. The solution is filled up to an end-volume of 10,000 ml with oxygen-free distilled water, filtered to give a completely clear filtrate and filled into brown-tinted 10 ml ampoules closed with a rubber stopper under carbon dioxide atmosphere. The ampoules are closed and sterilized at 100° C. for an hour.

| Preparation of Eye Drops | |
|---|---|
| Active Ingredient (Compound B) | 100.0 g |
| Sodium acetate | 27.0 g |
| Sodium chloride | 35.0 g |
| 0.1 N hydrochloric acid or 0.1N sodium hydroxide solution ad pH | 3.5–4.0 |
| Sodium pyrosulfite | 10.0 g |
| Distilled water ad | 10,000 ml |
| Preservative if necessary. | |

The sodium chloride, sodium acetate, sodium pyrosulfite and thereafter the active ingredient are dissolved in distilled water. The pH value of the solution (volume about 9500 ml) is adjusted to 3.5–4.0 with 0.1 N hydrochloric acid or 0.1 N sodium hydroxide. If necessary, 100 ml of 1% aqueous phenyl-mercury borate solution are added dropwise as preservative; thereafter the solution is filled up to an end-volume of 10,000 ml with distilled water. The solution is filtered germ-free under aseptic conditions and filled into 10 ml eyedrop glasses which are closed in a known manner.

| Preparation of Expectorants | |
|---|---|
| Active ingredient (Compound C) | 100.0 g |
| Citric acid, anhydrous | 6100 g |
| Glutaminium chloride | 3500 g |
| Lactose | 11000 g |
| Colloidal silicon dioxide | 180 g |
| Citric Oil | 100 g |
| Sodium o-benzoic acid sulfimide | 15 g |
| Saccharose | 400000 g. |

The first four components are ground and homogenized in a mill, whereafter the mixture of the fifth, sixth and seventh components, and finally the finely powdered saccharose is added. The mixture is stirred until homogeneous distribution of the components is achieved. 40 g of the mixture obtained are added to 200 ml calibrated bottles.

We claim:
1. A process for preparing a compound of the formula:

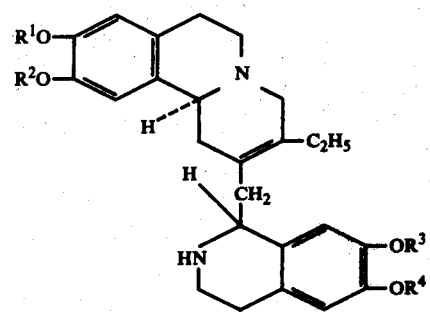

wherein
$R^1$ is the same as $R^2$ and each is lower alkyl and $R^3$ and $R^4$ are each lower alkyl, with the proviso that $R^1$ and $R^2$ are not methyl and $R^3$ and $R^4$ are not both ethyl, which comprises the steps of: reducing an unsaturated ester of the formula

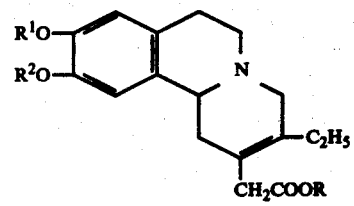

wherein R is a lower alkyl with diisobutyl-aluminum-hydride to an aldehyde of the formula:

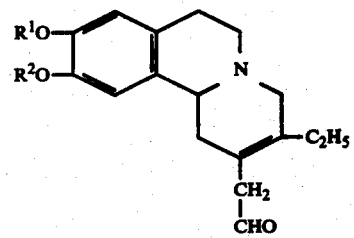

and condensing the compound thus obtained with β-(3-hydroxy-4-lower alkoxy-phenyl)-ethyl amine and alkylating the compound of the formula:

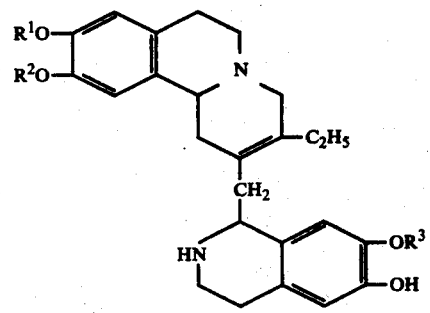

thus obtained.

2. A process for preparing a compound of the following formula:

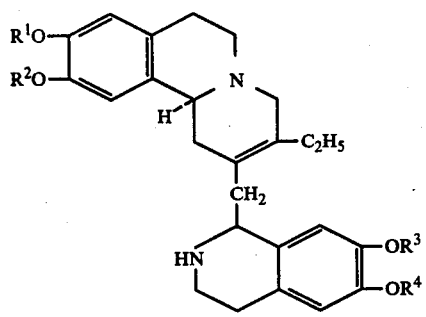

wherein
R¹ is the same as R² and each is lower alkyl and R³ and R⁴ are different from each other and are each lower alkyl, which comprises the steps of: reducing an unsaturated ester of the general formula:

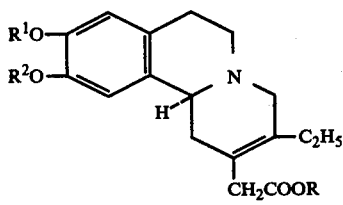

wherein R is a lower alkyl group, with diisobutyl-aluminum-hydride to an aldehyde of the formula:

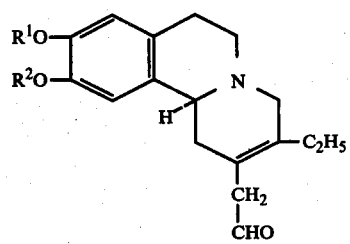

and condensing the compound thus obtained with β-(3-hydroxy-4-lower alkoxy-phenyl)-ethyl amine and alkylating the compound of the formula:

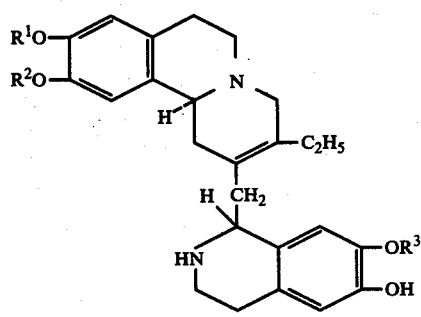

thus obtained.

* * * * *